United States Patent
Ohta et al.

(10) Patent No.: US 6,174,740 B1
(45) Date of Patent: *Jan. 16, 2001

(54) METHOD FOR ANALYZING IMPURITIES WITHIN SILICON WAFER

(75) Inventors: Yutaka Ohta, Gunma-ken; Hirofumi Nishijo; Akira Kosugi, both of Niigata-ken, all of (JP)

(73) Assignee: Shin-Etsu Handotai, Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/714,563

(22) Filed: Sep. 16, 1996

(30) Foreign Application Priority Data

Sep. 18, 1995 (JP) .................................. 7-264743

(51) Int. Cl.⁷ .................................. H01L 21/302
(52) U.S. Cl. .............. 438/14; 438/476; 438/477
(58) Field of Search .................. 134/13; 324/158 R; 438/14, 16, 17, 477, 471, 472, 473, 474, 475, 476, 759, 974, FOR 142, 946, 977, 966

(56) References Cited

U.S. PATENT DOCUMENTS 4,004,449   1/1977   Gorey et al. .
5,389,551 * 2/1995   Kamakura et al. ................ 438/476

FOREIGN PATENT DOCUMENTS 0 488 149   6/1992   (EP) .

OTHER PUBLICATIONS

Patent Abstracts of Japan, JP–A–06 249764 (Nippon Steel).

* cited by examiner

Primary Examiner—Savitri Mulpuri
(74) Attorney, Agent, or Firm—Snider & Associates; Ronald R. Snider

(57) ABSTRACT

A method for analyzing impurities within a silicon wafer in a convenient and simple manner with high accuracy and sensitivity.

In a first example 1, a silicon wafer is subjected on its surface to a sandblasting process with use of powder of $SiO_2$ and then to a thermal oxidation process in a dry-oxygen gas atmosphere to easily move impurities present within the silicon wafer into a distorted layer and to form a thermal oxide film and a surface layer of the wafer positioned directly therebelow and containing the distorted layer. The thermal oxide film or the surface layer containing the distorted layer is dissolved with, e.g., a solution of hydrofluoric acid to recover and analyze the dissolved solution. In a comparative example 1, the same processes as in the example 1 are carried out to analyze a predetermined solution, except that the sandblasting process is omitted. In a comparative example 2, the same processing steps as in the example 1 are carried out to analyze a predetermined solution, except that the formation of the thermal oxide film is replaced by a native oxide film without applying any heat. In both of the comparative examples 1 and 2, neither Ni nor Cu is detected; whereas, in the example 1, an Ni content is $100 \times 10^{10}$ atoms/cm² and a Cu content is $1 \times 10^{10}$ atoms/cm².

3 Claims, 2 Drawing Sheets

METHOD FOR ANALYZING IMPURITIES WITHIN SILICON WAFER

The present disclosure relates to subject matter contained in Japanese patent application No. 264743 (filed on Sep. 18, 1995) which is expressly incorporated herein by reference in its entirety.

BACKGROUND OF THE INVENTION

1. Field of the Invention

The present invention relates to a method for analyzing impurities contained within a silicon wafer in a simple manner with high accuracy and sensitivity.

2. Description of the Related Art

It is well known that, when there are present impurities such as metal elements (Al, Na, Fe, Cr, Ni, Cu, etc.) on or within a silicon wafer, these impurities have a harmful effect on electrical characteristics of a resultant semiconductor device. For this reason, it becomes essential to minimize or reduce the quantity of such impurities to a level as small as possible, which requires accurate analysis of the type, surface concentration and content of the impurities.

Conventional methods for directly analyzing metallic impurities on a silicon wafer or within a surface layer thereof include a secondary ion mass spectroscopy and a total reflection X-ray fluorescence analysis. In other matters, samples to be analyzed are taken from the surface layer of a silicon wafer. For example, a native oxide film on the surface layer of the silicon is dissolved with a vapor of hydrofluoric acid (HF), then a resultant dissolved solution is recovered as a sample, and then analyzed.

In both of these analysis methods, however, impurities present merely within the surface layer of the silicon wafer have been analyzed and it has been difficult to analyze impurities existing deep within the silicon wafer. Further, in the case where more impurities are contained deep within the wafer rather than the surface layer thereof or where the diffusion velocity of the impurities is fast, it has been impossible to attain its accurate quantitative evaluation.

Meanwhile, conventional methods for analyzing impurities in the bulk of a wafer include a method for analyzing a solution obtained by dissolving the entire wafer in a chemical agent solution and a secondary ion mass spectroscopy.

However, the former method has had a problem that not only a large quantity of the aforementioned solution is necessary with insufficient analysis accuracy and sensitivity but it also takes a lot of time to perform the analysis and the sample wafer is totally wasted. The latter method, on the other hand, has been disadvantageous in that expensive facilities are required and information obtained through a single sputtering analysis corresponds merely to that part of the sample which is as small as, e.g., 2 mm$^2$ (actually, a zone of 1 mm in diameter being able to be analyzed), which requires a lot of analysis time. In addition, the latter method is a destructive test.

SUMMARY OF THE INVENTION

It is therefore an object of the present invention to provide a method for analyzing impurities in the bulk of a silicon wafer which can analyze the impurities in the silicon wafer in a convenient and simple manner with high accuracy and high sensitivity and can suppress or minimize wastage and damage of a sample wafer, that is, the sample wafer being able to be used as an effective silicon wafer product.

In accordance with an aspect of the present invention, the above object is attained by providing a method of analyzing impurities in a bulk of a silicon wafer, which method comprises the steps of applying a mechanical damage onto one major surface of said silicon wafer to introduce distortions therein to form distorted layer, subjecting the silicon to a thermal oxidation process to form thermal oxide film on the wafer surface said distorted layer is formed thereon, dissolving the thermal oxide film or the thermal oxide film and surface layer of the wafer with a chemical solution or vapor to recover a dissolved solution, and analyzing the recovered solution.

In the invention, the step of subjecting the silicon wafer to the thermal oxidation process to form thermal oxide film on the wafer surface the distorted layer is formed thereon is carried out preferably by annealing the silicon wafer in the presence of an oxygen gas at a temperature of from 300° C. to 650° C. both inclusive for 2–120 minutes. Under these conditions, the formation of the thermal oxide film containing the distorted layer as well as the movement of the impurities within the silicon wafer into the distorted layer to be both promoted, thus allowing easy capture of the impurities. At temperatures less than 300° C., however, the movement velocity of the impurities within the silicon wafer becomes small, which requires a lot of time to realize sufficient capture of the impurities. At temperatures higher than 650° C., on the other hand, the diffusion velocity of the impurities within the silicon wafer becomes so fast that the diffusion energy is larger than the capture energy of the distorted layer, which makes it difficult to capture the impurities.

The reason why the time of the oxidation process is set in the aforementioned range is that a too short annealing time results in its insufficient capture effect and difficult evaluating of an absolute quantity of such impurities present within the wafer. A too long annealing time, on the other hand, results in reduction of its efficiency of the treatment and a fear of involving contamination from the outside even at the low temperature.

In accordance with another aspect of the present invention, there is provided a method of analyzing impurities in a bulk of a silicon wafer, which method comprises the steps of applying a mechanical damage onto one major surface of the silicon wafer to introduce distorted layer therein, converting the distorted layer at the surface of the wafer to a native oxide film (SiO$_2$ film) or a chemically-grown oxide film (SiO$_2$ film), subjecting the wafer to an annealing process at a temperature of from 300° C. to 650° C. both inclusive for 2–120 minutes, dissolving with a chemical solution or vapor any one selected from the group of (1) the native oxide film, (2) the native oxide film and the silicon surface layer directly therebelow, (3) the chemically-grown oxide film, and (4) the chemically-grown oxide film and the silicon surface layer directly therebelow to recover the dissolved solution, and analyzing the recovered solution.

In this connection, the above native oxide film is formed by a known method, for example, by keeping the silicon wafer in an atmosphere having a normal temperature and a normal pressure. The above "chemically-grown oxide film" can be formed, for example, by immersing a silicon wafer in a mixed solution of hydrogen peroxide, ammonia and water which is used at the time of cleaning the silicon wafer.

In this invention, when the silicon wafer is subjected to an annealing process at a temperature of from 300° C. to 650° C. both inclusive for 2–120 minutes, the impurities in the bulk of the silicon wafer are moved into either one or both of the distorted layer and oxide film.

In accordance with yet another aspect of the present invention, there is provided a method of analyzing impurities in a bulk of a silicon wafer, which method comprises the steps of applying a mechanical damage onto one major surface of the silicon wafer to introduce distortions therein to form distorted layer, subjecting the distorted layer at the surface of the silicon wafer to an atmospheric pressure chemical vapor deposition (CVD) process or a low pressure CVD process to deposit an oxide film ($SiO_2$ film) on the distorted layer, dissolving the oxide film or the oxide film and the surface layer of the wafer with a chemical solution or vapor to recover a dissolved solution, and analyzing the recovered solution.

In the present invention, the above step of depositing the oxide film is carried out preferably at a temperature of from 300° C. to 650° C. both inclusive for 2–120 minutes. At temperatures less than 300° C., the movement velosity of the impurities within the silicon wafer becomes small. At temperatures higher than 650° C., on the other hand, the diffusion velosity of the impurities becomes so fast that the diffusion energy is larger than the capture energy of the distorted layer, which makes it difficult to capture the impurities in the distortion layer of the silicon wafer.

The reason why the processing time of the CVD process is set in the aforementioned range is that a too short processing time results in its insufficient capture effect and difficult evaluating of an absolute quantity of such impurities present within the wafer. A too long processing time, on the other hand, results in its reduced processing efficiency and a fear of involving contamination from the outside even at the low temperature.

In the above aspects, the method for applying a mechanical damage onto the silicon wafer can be implemented by sandblasting, by lapping or by laser irradiation. The sandblasting is carried out by blasting based on collision of granules and/or powders of like dry ice, pure water, aqueous acid solution, organic substance being solid state at a temperature range between −20 to 10° C. and being liquid at temperatures exceeding 10° C. and so on.

Whether to apply the mechanical damage to a side (front side) of the silicon wafer where a semiconductor device is to be formed or to the opposite side (rear side) thereof, it is determined preferably by taking into consideration a bulk impurity recovery rate into the chemical solution or vapor for the dissolution process.

In the present invention, as the chemical solution for dissolving only the aforementioned thermal oxide film, the aforementioned native oxide film, chemically-grown oxide film or oxide film deposited by the CVD process or one of these oxide films and the silicon surface layer positioned directly therebelow; a well-known etching solution may be employed. In the former case, it is preferable that the chemical solution be, for example, hydrofluoric acid; whereas, in the latter case, it is preferable that the chemical solution be, for example, a mixed solution of hydrofluoric acid, nitric acid and acetic acid.

Even in the case of either one of qualitative and quantitative analysis of the bulk impurities, it is desirable to bring into contact with the etching solution the entire area of oxide film (thermal oxide film, native oxide film, chemically-grown oxide film or deposited oxide film) of the sample wafer as well as the entire surface layer of the silicon wafer positioned immediately therebelow. This is for the purpose of increasing a recovery rate of bulk impurities into the chemical solution for wafer dissolution process. To this end, there are suggested, for example, methods (1) and (2) which follow.

That is,
(1) a sample wafer is placed within a sealed container, the aforementioned mixed etching solution is supplied in the form of vapor onto the entire surface of a thermal oxide where it is condensed.
(2) A sample wafer is placed within a sealed container, a vapor of hydrofluoric acid is supplied onto the entire surface of a thermal oxide film to be condensed and to make the wafer surface hydrophobic, and then the aforementioned etching mixture solution is dropped onto the surface of the sample to be movingly contacted with all over the sample surface (refer to Japanese Patent Laid-Open Publication No. 2-28533, entitled "Impurity Measuring Method & Measuring Device").

In the present invention, the completion of dissolution of only the oxide film of the sample wafer can be confirmed, when a hydrofluoric acid solution is employed as the chemical solution for dissolution of the oxide film for example, based on the fact that the wafer surface becomes hydrophobic with the progress of the dissolution of oxide, then the acid solution is repelled by the resultant silicon wafer surface to form a liquid sphere, although the wafer surface is hydrophilic under the presence of the oxide film.

Further, the completion of dissolution of the silicon surface layer positioned directly below the oxide film can be confirmed by measuring the thickness of the silicon wafer at proper times to confirm that a difference between the thicknesses of the wafer before and after the dissolution becomes sufficiently large.

BRIEF DESCRIPTION OF THE DRAWINGS

The above and other objects, features and advantages of the present invention will become apparent from the following detailed description when taken with the accompanying drawings in which.

DESCRIPTION OF THE PREFERRED EMBODIMENTS

The present invention will be detailed in connection with several preferred embodiments.

Figure 1A:
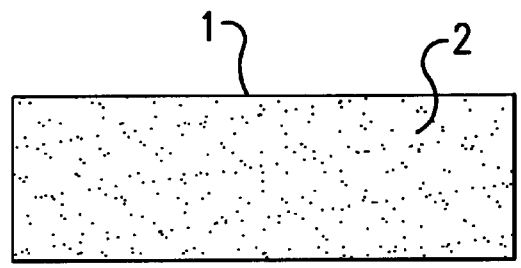
FIGS. 1a–1d shows cross-sectional views for explaining processing steps and operations in a method for analyzing impurities in the bulk of a silicon wafer in accordance with a first invention.
Figure 1B:
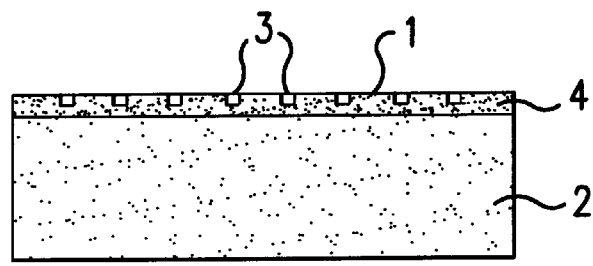
Figure 1C:
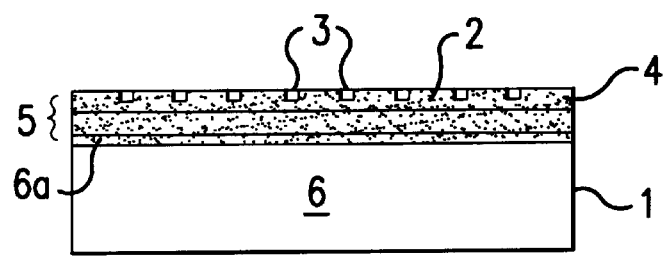

In first one of the embodiments of the present invention, a silicon wafer 1 containing impurities 2 therein as shown in FIG. 1a is formed in its one major surface with such distortions 3 to form a distorted layer 4 thereon as shown in FIG. 1b. As shown in FIG. 1c, a surface layer of the silicon wafer 1 positioned on its distortions-introduced side is subjected to a thermal oxidation process to form a thermal oxide film 5 thereon. Thus, the distorted layer 4 forms the surface layer of the thermal oxide film 5. Under the influence of the thermal energy, the impurities 2 present in the bulk under a boundary surface between the thermal oxide film 5 and a silicon layer 6 are moved through the silicon and captured within the distorted layer 4; while the impurities 2 present on the above boundary, in the vicinity thereof, or in the layer thereabove are moved into the thermal oxidation film 5 or to the boundary.

Figure 1D:
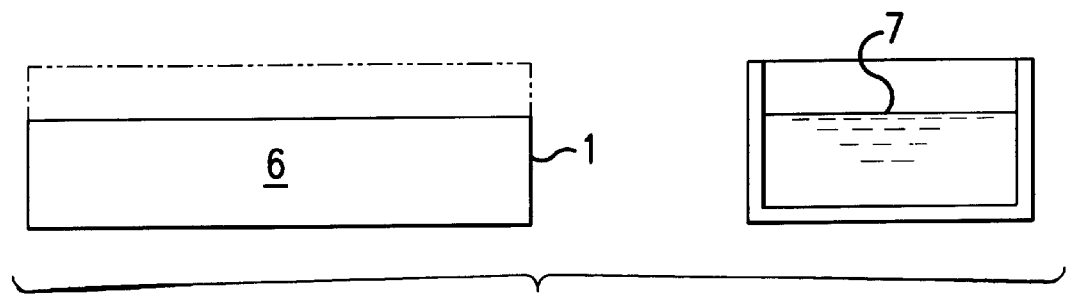

Accordingly, as shown in FIG. 1d, the thermal oxide film 5 and an surface layer 6a positioned directly therebelow as an upper surface of the silicon layer 6 are dissolved with a chemical solution to recover a dissolution solution 7. When the dissolution solution 7 is analyzed, a total quantity of impurities attached onto the surface of the silicon wafer 1, impurities adsorbed on the surface of the silicon wafer 1, and the bulk impurities 2 can be quantitatively analyzed with high accuracy and high sensitivity.

When only the thermal oxide film 5 is dissolved and removed from the wafer, an impurity recovery rate slightly drops compared to that in FIG. 1.

In the analysis method of the first invention, since only the surface layer of the sample wafer is converted to the thermal oxide film, and the thermal oxide film and the surface layer of the silicon layer are dissolved and removed; it takes less time to get an analysis sample solution. Further, since a less quantity of such analysis sample, that is, a less quantity of predetermined dissolution solution is required; sufficient analysis accuracy and sensitivity can be realized.

In addition, the thickness of the wafer after the analysis sample is taken is made thinner by an amount corresponding nearly to the thickness of the thermal oxide film than that before the sample is taken. Since almost all the surface and bulk impurities are removed and thus the wafer exhibits excellent electrical characteristics, however, this analysis method is advantageous in that there can be obtained a high quality of wafer which contains substantially no impurities removed simultaneously with the taking of the analysis sample.

In an analysis method of the second invention, a native oxide film or a chemically-grown oxide film in place of the thermal oxide film 5 is formed and then subjected to an annealing process under predetermined conditions, producing substantially the same action and effect as in the first embodiment.

Figure 2A:
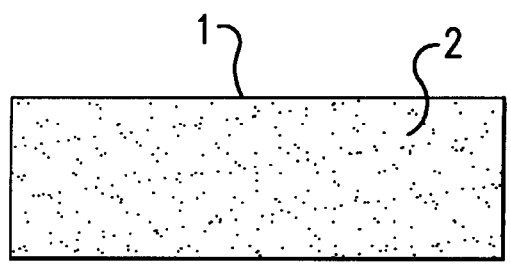
FIG. 2a–2d shows cross-sectional views for explaining processing steps and operations in a method for analyzing impurities in the bulk of a silicon wafer in accordance with a third invention.
Figure 2B:
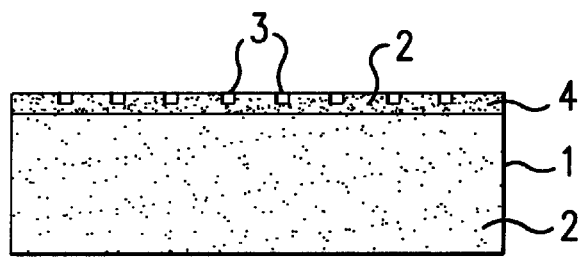
Figure 2C:
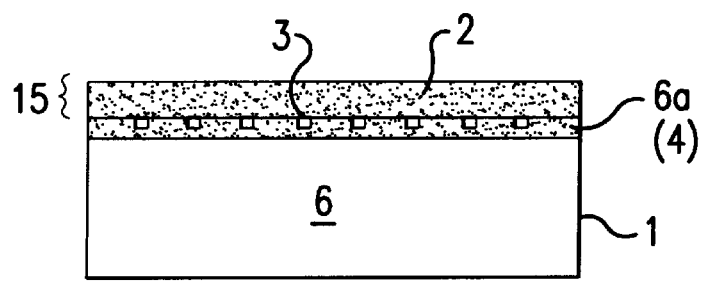

In an analysis method of the third invention, a silicon wafer 1 containing internal impurities 2 therein as shown in FIG. 2a is formed in its one major surface with such distortions 3 as shown in FIG. 2b. As shown in FIG. 2c, thermal energy when an oxide film 15 is formed on a major surface of the silicon wafer 1 positioned on its distortions-introduced side causes impurities 2 present in the bulk of a silicon layer 6 to move into a boundary between the oxide film 15 and silicon layer 6 or into the oxide film 15.

Figure 2D:
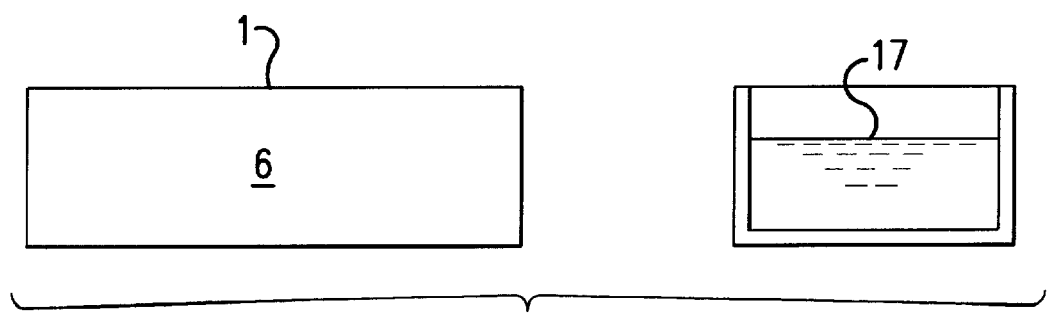

Accordingly, as shown in FIG. 2d, the oxide film 15 and an surface layer 6a positioned directly therebelow as an upper surface of the silicon layer 6 are dissolved with a chemical solution to recover a dissolution solution 17. When the dissolution solution 17 is analyzed, a total quantity of impurities attached onto the surface of the silicon wafer 1, impurities adsorbed on the surface of the silicon wafer 1, and the internal impurities 2 can be quantitatively and qualitatively analyzed with relatively high accuracy and high sensitivity.

In an analysis method of the third invention, since an oxide film is formed on a sample wafer, and the oxide film and the surface layer of the silicon layer positioned directly therebelow are dissolved and removed; it takes less time to get an analysis sample solution. Further, since a less quantity of such analysis sample, i.e., a less quantity of predetermined dissolution solution is required; sufficient analysis accuracy and sensitivity can be realized.

Further, the thickness of the remaining sample wafer after the analysis sample is taken is not made substantially thinner than that before the sample is taken. Furthermore, since almost all the surface and bulk impurities are removed and thus the wafer exhibits excellent electrical characteristics, this analysis method is advantageous in that there can be obtained a high quality of wafer which contains substantially no impurities removed simultaneously with the taking of the analysis sample.

An example of the present invention and comparative examples will be detailed below.

EXAMPLE 1

Prepared as samples were a plurality of silicon wafers of a p type <100> having a diameter of 200 mm and a thickness of 725 $\mu$m obtained through exactly the same steps. One was selected from the prepared samples, subjected on its one side to a sandblasting process with use of powder of $SiO_2$, and then subjected to an oxidation process for 10 minutes in an oxygen atmosphere with a dryness of 100% and a temperature of 430° C., which resulted in that the sandblasted side of the silicon wafer was formed thereon with a thermal oxide film as a wafer surface layer. The thermal oxide film was dissolved with a solution of hydrofluoric acid to obtain a solution, the solution was recovered, and then subjected by a flameless atomic absorption spectrometer to a quantitative analysis of metal elements contained therein.

As a result of the quantitative analysis, an Ni content was $100 \times 10^{10}$ atoms/$cm^2$ and a Cu content was $1 \times 10^{10}$ atoms/$cm^2$.

Comparative Example 1

One was selected from the remaining silicon wafer samples other than the used sample and subjected to exactly the same processes as in the Example 1, except that the sandblasting process with use of the powder of $SiO_2$ was not used An obtained thermal oxide film was dissolved with a solution of hydrofluoric acid to obtain a solution, the solution was recovered and then subjected by the flameless atomic absorption spectrometer to qualitative and quantitative analysis of metal elements contained therein.

As a result of the analysis, neither Ni nor Cu was detected.

Comparative Example 2

One was selected from the silicon wafer samples remaining in the Example 1, subjected on its one side to a sandblasting process with use of powder of $SiO_2$ in the same manner as in the Example 1, and then left to stand in a clean booth to grow a native oxide film on the wafer. The native oxide film was dissolved with a solution of hydrofluoric acid, the resultant solution was recovered, and subjected by flameless atomic absorption spectrometer to a quantitative analysis of metal elements contained therein.

As a result of the analysis, neither Ni nor Cu was detected.

As will be clear from the foregoing explanation, in accordance with a first invention, since a mechanical damage is applied to one major surface of a silicon wafer to introduce distortions therein and then the silicon wafer is subjected to a thermal oxidation process; impurities in the bulk of the silicon wafer can be collected in the oxide film and the surface layer (distortion zone) of the silicon wafer positioned directly therebelow. Further, since the thermal oxide film or the thermal oxide film and the surface layer of the silicon wafer positioned directly therebelow are dissolved with a chemical liquid to recover and analyze the dissolution solution; the impurities within the wafer can be advantageously analyzed in a convenient and simple manner with high accuracy and sensitivity.

In accordance with a second invention, since impurities in the bulk of a silicon wafer are moved into a native oxide film formed as a surface layer of the wafer and also into a surface layer of the wafer positioned directly therebelow to prepare and analyze a predetermined solution in substantially the same manner as in the first invention; the second invention can exhibit substantially the same effects as the first invention.

In accordance with a third invention, since impurities within a silicon wafer are moved through the silicon wafer under the influence of thermal energy during the chemical vapor deposition (CVD) process over a distorted layer to be formed on the surface layer of the wafer, that is, since the impurities are moved into a deposited oxide film and the surface layer (distorted layer) of the wafer positioned directly therebelow to prepare and analyze a predetermined solution in substantially the same procedure as in the first invention; the third invention can exhibit substantially the same effects as the first invention.

While the present invention has been described in connection with certain preferred embodiments, it is to be understood that the subject matter encompassed by the present invention is not limited to those specific embodiments. On the contrary, it is intended to include all alternatives, modifications, and equivalents as can be included within the spirit and scope of the following claims.

What is claimed is:

1. A method of analyzing impurities in a bulk of a silicon wafer, comprising the steps of:

applying a mechanical damage onto one major surface of said silicon wafer to introduce distortions therein to form distorted layer;

subjecting the silicon wafer to a thermal oxidation process to form a thermal oxide film on the wafer surface where said distorted layer is formed thereon;

dissolving only said thermal oxide film with a chemical solution or vapor to recover a dissolved solution; and analyzing said recovered solution; and determining bulk impurities of the wafer;

wherein said step of subjecting the silicon wafer to a thermal oxidation process to form thermal oxide film on the wafer surface said distorted layer is formed thereon is carried out by annealing said silicon wafer in the presence of an oxygen gas at a temperature of from 300° C. to 650° C. both inclusive for 2–120 minutes.

2. A method of analyzing impurities in a bulk of a silicon wafer, comprising the steps of:

applying a mechanical damage onto one major surface of said silicon wafer to introduce distortions therein to form a distorted layer;

converting said distorted layer at the surface of the silicon wafer to a native or chemically-grown oxide film;

subjecting the wafer to an annealing process at a temperature of from 300° C. to 650° C. both inclusive for 2–120 minutes;

dissolving with a chemical solution or vapor only any one selected from the group consisting of (1) said native oxide film, and (2) said chemically-grown oxide film to recover a dissolved solution;

analyzing said recovered solution; and determining bulk impurities of the wafer.

3. A method of analyzing impurities in a bulk of a silicon wafer, comprising the steps of:

applying a mechanical damage onto one major surface of said silicon wafer to introduce distortions therein to form a distorted layer;

subjecting said distorted layer at the surface of the silicon wafer to an atmospheric pressure chemical vapor deposition (CVD) process or a low pressure CVD process at a temperature of from 300° C. to 650° C. both inclusive for 2–120 minutes to deposit an oxide film on said distorted layer;

dissolving said oxide film with a chemical solution or a vapor to recover a dissolved solution;

analyzing said recovered solution; and determining bulk impurities of the wafer.

* * * * *